United States Patent
Schulze Zur Wiesche

(10) Patent No.: US 11,213,476 B2
(45) Date of Patent: Jan. 4, 2022

(54) METHOD FOR GENTLE, CHEMICAL HAIR TREATMENT

(71) Applicant: Henkel AG & Co. KGaA, Duesseldorf (DE)

(72) Inventor: Erik Schulze Zur Wiesche, Hamburg (DE)

(73) Assignee: HENKEL AG & CO. KGAA, Duesseldorf (DE)

( * ) Notice: Subject to any disclaimer, the term of this patent is extended or adjusted under 35 U.S.C. 154(b) by 126 days.

(21) Appl. No.: 16/675,417

(22) Filed: Nov. 6, 2019

(65) Prior Publication Data
US 2020/0138694 A1 May 7, 2020

(30) Foreign Application Priority Data

Nov. 7, 2018 (DE) .................... 10 2018 218 945.5

(51) Int. Cl.
A61K 8/898 (2006.01)
A61Q 5/10 (2006.01)
A61Q 5/04 (2006.01)
A61K 8/34 (2006.01)
A61K 8/33 (2006.01)
A61K 8/86 (2006.01)
A61K 8/365 (2006.01)

(52) U.S. Cl.
CPC .............. A61K 8/898 (2013.01); A61K 8/33 (2013.01); A61K 8/345 (2013.01); A61K 8/365 (2013.01); A61K 8/86 (2013.01); A61Q 5/04 (2013.01); A61Q 5/10 (2013.01); A61K 2800/43 (2013.01); A61K 2800/884 (2013.01)

(58) Field of Classification Search
CPC .......... A61K 2800/43; A61K 2800/884; A61K 8/898; A61K 8/86; A61Q 5/04; A61Q 5/10
See application file for complete search history.

(56) References Cited

U.S. PATENT DOCUMENTS

| 4,834,791 A | 5/1989 | Axelsson et al. | |
| 4,834,971 A * | 5/1989 | Klenk | A61K 8/26 424/70.4 |
| 8,740,995 B1 * | 6/2014 | Schweinsberg | A61Q 5/004 8/405 |
| 8,790,417 B2 * | 7/2014 | Schweinsberg | A61K 8/25 8/405 |
| 8,814,952 B2 * | 8/2014 | Schweinsberg | A61K 8/585 8/405 |
| 8,900,329 B2 * | 12/2014 | Schulze zur Wiesche | A61K 8/898 8/405 |
| 2014/0017010 A1 | 1/2014 | Jones | |
| 2014/0170100 A1 * | 6/2014 | Schweinsberg | A61K 8/898 424/62 |
| 2018/0000701 A1 * | 1/2018 | Schulze zur Wiesche | A61Q 5/04 |

FOREIGN PATENT DOCUMENTS

| EP | 1923048 A1 | 5/2008 | |
| GB | 2557378 A | 6/2018 | |
| WO | WO 2016/096449 | * 6/2016 | ............... A61Q 5/04 |

* cited by examiner

Primary Examiner — Anna R Falkowitz
(74) Attorney, Agent, or Firm — Lorenz & Kopf, LLP

(57) ABSTRACT

The application describes a cosmetic method for the chemical treatment of keratinic fibers, in which
  i. a cosmetic composition is applied as a pretreatment agent to keratinic fibers, and
  ii. the keratinic fibers are subjected to a chemical treatment with an oxidizing agent and/or a reducing agent within a period of from about 5 seconds to about 24 hours after step i., wherein the cosmetic composition, based on its total weight, comprises from about 0.01 to about 4.00% by weight of a polyorganosiloxane of the formula (I)

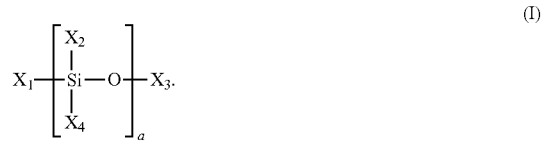

(I)

The damage to the keratinic fibers due to the oxidizing and/or reducing agents can be reduced by using the special pretreatment agent.

19 Claims, No Drawings

METHOD FOR GENTLE, CHEMICAL HAIR TREATMENT

CROSS-REFERENCE TO RELATED APPLICATION

This application claims priority to German Patent Application No. 10 2018 218 945.5, filed Nov. 7, 2018, which is incorporated herein by reference in its entirety.

TECHNICAL FIELD

The present disclosure is in the field of cosmetics and relates to a method of reducing damage in the chemical treatment of keratinic fibers, in which a cosmetic composition is applied to keratinic fibers as a pretreatment agent prior to the chemical hair treatment.

BACKGROUND

Hair can be damaged by natural or artificially induced processes. The natural processes can, for example, have a combined (for example, simultaneous) action of UV light and oxygen ($O_2$) on the hair. The artificially induced processes can comprise, for example, applying hair dye (also referred to as colorations), bleaching and/or generating a permanent wave.

In addition to desirable cosmetic effects, such as a lightening of the hair, it is also possible for severe damage to the hair to occur, for example, when using oxidizing agents.

The resulting damage type is called oxidative damage and is caused by the use of colorations, bleaching, permanent waving and also by environmental influences ($UV+O_2$). This damage is caused by the oxidation of the amino acids cystine and cysteine, which are common in the hair, to cysteic acid.

Cystine can form intermolecular disulfide bridges (also called SS bridges) in the hair, so that the cystine is extremely important for the mechanical stability of the hair.

Oxidation of these bridges to cysteic acid can destroy the mechanical stability of the hair and even lead to complete hair breakage with multiple applications. However, previously macroscopically perceptible, for example, tangible, properties of the hair, for example, a surface roughness, can be negatively influenced.

In addition to this oxidative damage, reductive damage to the hair is also possible. This occurs in cosmetic methods that use reducing agents. These are, for example permanent waves or chemical smoothing methods, which contain reducing agents such as thioglycolic acid or sulfite. These ingredients are used to open the disulfide bridges of cysteine for the purpose of reshaping the hair. The following sulfur species are formed in this case: R—S—H (thiols), R—S—$SO_3^-$, (bunte salts, after sulfite treatment), R—S—S—$CH_2COO^-$ (disulfides with thiglycolate units, after thioglycolate treatment).

A method for oxidative hair treatment is known from EP 1923048 A1 in which a cosmetic agent containing a plant extract combination from at least two different plant extracts is first applied to keratinic fibers and then an oxidative cosmetic agent containing an oxidizing agent is applied. Pre-treatment with the cosmetic agent containing a plant extract combination reduces the oxidative damage caused by the use of the oxidizing agent.

However, the methods known in the art do not always result in a desired degree of reduced hair damage.

BRIEF SUMMARY

Methods for the chemical treatment of keratinic fibers are provided. In an exemplary embodiment, a method for the chemical treatment of keratinic fibers includes: i.) applying a cosmetic composition to the keratinic fibers as a pretreatment; and ii.) chemically treating the keratinic fibers with an oxidizing agent and/or a reducing agent within a period of from about 5 seconds to about 24 hours after step i.) The cosmetic composition includes a polyorganosiloxane of formula (I) from about 0.1 to about 4.0 weight percent.

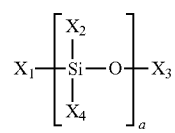

Another method of chemically treating keratinic fibers is provided in another embodiment. The method includes applying a cosmetic composition to the keratinic fibers as a pretreatment, wherein the cosmetic composition includes Amodimethicone/Morpholinomethyl Silsesquioxane Copolymer. The cosmetic composition is left on the keratinic fibers at least until the keratinic fibers are chemically treated with an oxidizing agent, where the keratinic fibers are chemically treated within about 5 seconds to about 24 hours after the pretreatment. A further cosmetic composition is applied to the keratinic fibers as a post-treatment after the chemical treatment, where the further cosmetic composition has a pH of from about 3 to about 5, and includes a metal salt selected from strontium salts, zirconium salts, hafnium salts, titanium salts, tin salts, aluminum salts, bismuth salts, lanthanum salts, calcium salts, magnesium salts, and mixtures thereof.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

It is an object of the present disclosure to therefore provide a cosmetic method for the treatment of keratinic fibers, which leads to a significantly reduced damage in the chemical treatment of keratinic fibers. The method should be easy and quick to perform.

This object is achieved by a cosmetic method for the chemical treatment of keratinic fibers, in which i. a cosmetic composition is applied as a pretreatment agent to keratinic fibers, and ii. the keratinic fibers are subjected to a chemical treatment with an oxidizing agent and/or a reducing agent within a period of from about 5 seconds to about 24 hours after step i., exemplified in that the cosmetic composition, based on its total weight, comprises from about 0.01 to about 4.00% by weight of a polyorganosiloxane of the formula (I)

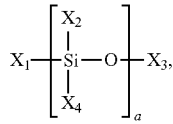

wherein $X_1$ and $X_2$ independently of one another mean OH, $OR^1$, $R^2$, O-PDMS or O-fSiloxane, $X_3$ denotes hydrogen or a monovalent hydrocarbon radical having 1 to 8 carbon atoms per radical, PDMS or fSiloxane, $X_4$ is a radical of the formula

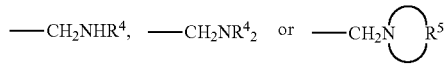

and a is an integer from 1 to about 100, wherein $R^1$ denotes an alkyl radical having 1 to 8 carbon atoms, $R^2$ denotes a monovalent, saturated or unsaturated hydrocarbon radical having 1 to about 200 carbon atoms per radical, optionally substituted with the elements N, P, S, O, Si and halogen, PDMS stands for

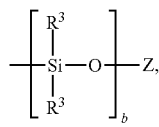

fSiloxane stands for

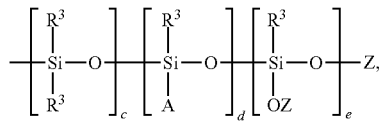

$R^3$ independently of one another each denotes a monovalent, saturated or unsaturated hydrocarbon radical having 1 to about 200 carbon atoms per radical, optionally substituted with the elements N, P, S, O, Si and halogen, A denotes a radical of the formula $R^6$—[$NR^7$—$R^8$-]$_f NR^7{}_2$, wherein $R^6$ denotes a divalent linear or branched hydrocarbon radical having 3 to about 18 carbon atoms, $R^7$ denotes a hydrogen atom, an alkyl group having 1 to 8 carbon atoms or an acyl radical, $R^8$ denotes a divalent hydrocarbon radical having 1 to 6 carbon atoms, b is an integer from 1 to about 2000, c is 0 or a number from 1 to about 2000, d is an integer from 1 to about 1000, e is 0 or a number from 1 to 5.

f is 0, 1, 2, 3 or 4,

Z denotes hydrogen, an alkyl radical having 1 to 8 carbon atoms or

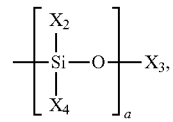

$R^4$ denotes a monovalent hydrocarbon radical having 1 to about 18 carbon atoms, optionally containing N and/or O atoms, and $R^5$ denotes a divalent hydrocarbon radical having 3 to about 12 carbon atoms, optionally containing N and/or O atoms.

It has now surprisingly been found that a method in which a particular cosmetic composition is applied to the keratinic fibers prior to the chemical treatment leads to reduced hair damage, whereby less roughness, split ends or hair breakage occur. Accordingly, the method as contemplated herein is a cosmetic method for gentle, chemical treatment of keratinic fibers.

In a preferred embodiment, the cosmetic composition is not washed off or rinsed out before method step ii. is performed.

The keratinic fibers can be optionally dried after performing the treatment step i.

In a particularly preferred embodiment, keratinic fibers are dried after carrying out the treatment step i, preferably by supplying warm air. It has been found that the adhesion of the polyorganosiloxanes of the formula (I) on the keratinic fibers is improved by the drying step. Without wishing to be bound by this theory, the drying step triggers condensation reactions between the polyorganosiloxanes of the formula (I), which in turn lead to improved adhesion of the condensed polyorganosiloxanes to the keratinic fibers.

As contemplated herein, keratin-containing or keratinic fibers are understood to mean furs, wool. feathers and in particular human hair.

The cosmetic composition comprises at least one polyorganosiloxane of the formula (I).

In addition, the aforementioned use enhances the suppleness and softness of the keratinic fibers after dyeing and/or bleaching without undesirable fiber weighting.

Particularly suitable are polyoranosiloxanes of the formula (I)

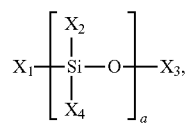

wherein $X_1$ and $X_2$ independently of one another denote OH, $OR^1$, $R^2$, O-PDMS or O-fSiloxane, $X_3$ denotes hydrogen or a monovalent hydrocarbon radical having 1 to 8 carbon atoms per radical, PDMS or fSiloxane,
$X_4$ is a radical of the formula

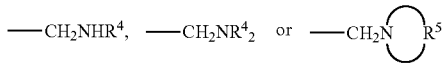

and
a is a number from 1 to about 100, preferably a number from 1 to 5,
wherein
$R^1$ denotes an alkyl radical having 1 to 8 carbon atoms,
$R^2$ denotes a monovalent, saturated or unsaturated hydrocarbon radical having 1 to about 200 carbon atoms per radical, optionally substituted with the elements N, P, S, O, Si and halogen, PDMS stands for

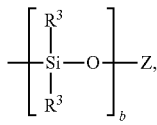

fSiloxane stands for

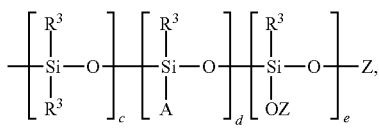

$R^3$ independently of one another each denotes a monovalent, saturated or unsaturated hydrocarbon radical having 1 to about 200 carbon atoms per radical, optionally substituted with the elements N, P, S, O, Si and halogen,
A denotes a radical of the formula $R^6-[NR^7-R^8-]_fNR^7_2$, wherein
$R^6$ denotes a divalent linear or branched hydrocarbon radical having 3 to about 18 carbon atoms,
$R^7$ denotes a hydrogen atom, an alkyl group having 1 to 8 carbon atoms or an acyl radical,
$R^8$ denotes a divalent hydrocarbon radical having 1 to 6 carbon atoms,
b is a number from 1 to about 2000, preferably from 1 to about 1000,
c is 0 or a number from 1 to about 2000, preferably from about 50 to about 1000,
b is a number from 1 to about 1000, preferably from 1 to about 10,
e is 0 or a number from 1 to 5,
f is 0, 1, 2, 3 or 4,
Z denotes hydrogen, an alkyl radical having 1 to 8 carbon atoms or

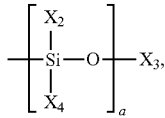

$R^4$ denotes a monovalent hydrocarbon radical having 1 to about 18 carbon atoms, optionally containing N and/or O atoms, and $R^5$ denotes a divalent hydrocarbon radical having 3 to about 12 carbon atoms, optionally containing N and/or O atoms.

Examples of an alkyl radical $R^1$ are methyl, ethyl, n-propyl, iso-propyl, 1-n-butyl, 2-n-butyl, iso-butyl, tert.-butyl, n-pentyl, iso-pentyl, neo-pentyl, tert.-pentyl, n-hexyl, n-heptyl, n-octyl, iso-octyl or 2,2,4-trimethylpentyl, wherein methyl, ethyl and butyl are preferred.

Examples of hydrocarbon radicals $R^2$ and $R^3$ are alkyl radicals, such as methyl, ethyl, n-propyl, iso-propyl, 1-n-butyl, 2-n-butyl, iso-butyl, tert.-butyl, n-pentyl, iso-pentyl, neo-pentyl, tert.-pentyl, n-hexyl, n-heptyl, n-octyl, iso-octyl, 2,2,4-trimethylpentyl, n-nonyl, n-decyl, n-dodecyl, n-octadecyl, cyclopentyl, cyclohexyl, cycloheptyl, methylcyclohexyl, vinyl, 5-hexenyl, cyclohexenyl, 1-propenyl, allyl, 3-butenyl, 4-pentenyl, phenyl, naphthyl, anthryl, phenanthryl, o-tolyl, m-tolyl, p-tolyl, xylyl, ethylphenyl, benzyl, alpha-phenylethyl and beta-phenylethyl radicals. The methyl, ethyl, octyl and phenyl radical are preferred as radical $R^2$, particularly preferred are the methyl and ethyl radical.

Examples of halogenated radicals $R^2$ and $R^3$ are the 3,3,3-trifluoro-n-propyl, 2,2,2',2',2'-hexafluoroisopropyl, heptafluoroisopropyl, o-chlorophenyl, m-chlorophenyl and p-chlorophenyl radical.

Examples of $R^4$ are the alkyl, cycloalkyl, aryl, alkaryl and aralkyl radicals listed for the hydrocarbon radicals $R^2$ and $R^3$.

Preferred examples of $R^5$ are radicals of the formulas $-CH_2-CH_2-O-CH_2-CH_2-$, $-CH_2-CH_2-NH-CH_2-CH_2-$ or $-CH_2-CH_2-NH-CH_2-$, wherein the radical $-CH_2-CH_2-O-CH_2-CH_2-$ is particularly preferred.

Examples of $R^6$ are alkylene radicals having 3 to about 10 carbon atoms such as propylene, butylene, pentylene, hexylene, heptylene, octylene, nonylene and decylene.

$R^7$ can be a hydrogen atom, a methyl, ethyl, n-propyl, iso-propyl, 1-n-butyl, 2-n-butyl, iso-butyl, tert.-butyl, n-pentyl, iso-pentyl, neo-pentyl, tert.-pentyl, n-hexyl, n-heptyl, n-octyl, iso-octyl, 2,2,4-trimethylpentyl or acetyl radical, wherein a hydrogen atom is preferred.

Preferred examples of $R^8$ are alkylene radicals such as methylene, ethylene, propylene, butylene, pentylene, or hexylene.

Z is preferably hydrogen or methyl, ethyl, n-propyl, iso-propyl, 1-n-butyl, 2-n-butyl, iso-butyl, tert.-butyl, n-pentyl, iso-pentyl, neo-pentyl, tert.-pentyl, n-hexyl, n-heptyl, n-octyl, iso-octyl or 2,2,4-trimethylpentyl, wherein hydrogen, methyl, ethyl and butyl are particularly preferred.

Preferred radicals $X_4$ are, in accordance with the above definitions for $R^4$ and $R^5$, aminomethyl, methylaminomethyl, dimethylaminomethyl, diethylaminomethyl, dibutylaminomethyl, cyclohexylaminomethyl, morpholinomethyl, piperidinomethyl, piperazinomethyl, ((diethoxymethylsilyl)methyl)cyclohexylaminomethyl, ((triethoxysilyl)methyl)cyclohexylaminomethyl, anilinomethyl, 3-dimethylaminopropyl-aminomethyl, or bis(3-dimethylaminopropyl) aminomethyl radicals and mixtures thereof. In this case, it is highly preferred when the hair treatment agent contains polyorganosiloxanes of the formula (I) which contain the morpholinomethyl radical as radical $X_4$.

According to the definitions for $R^6$, $R^7$ and $R^8$, preferred examples of radical A are:
$-(CH_2)_3NH_2$
$-(CH_2)_3-NH-(CH_2)_2-NH_2$
$-CH_2CH(CH_3)CH_2-NH-(CH_2)_{12}-NH_2$
$-(CH_2)_3-NH(cyclohexyl)$
$-(CH_2)_3-NHCH_3$ —(CH$_2$)$_3$—N(CH$_3$)$_2$
—(CH$_2$)$_3$—NHCH$_2$CH$_3$
—(CH2)$_3$—N(CH$_2$CH$_3$)$_2$
—(CH$_2$)$_4$—NH$_2$
—CH$_2$CH(CH$_3$)CH$_2$—NH$_2$
—(CH$_2$)$_3$—NH—(CH$_2$)$_2$—NHCH$_3$
—(CH$_2$)$_3$—NH—(CH$_2$)$_2$—N(CH$_3$)$_2$
—(CH$_2$)$_3$—NH—(CH$_2$)$_2$—NHCH$_2$CH$_3$
—(CH$_2$)$_3$—NH—(CH$_2$)$_2$—N(CH$_2$CH$_3$)$_2$
—(CH$_2$)$_3$[—NH—CH$_2$CH$_2$]$_2$—NH$_2$
—(CH$_2$)$_3$—NH(acetyl)
—(CH$_2$)$_3$—NH—(CH$_2$)$_2$—NH(acetyl) and
—(CH$_2$)$_3$—N(acetyl)-(CH$_2$)$_2$—NH(acetyl).

For the preparation of the polyorganosiloxanes of the formula (I), commercially available polydimethylsiloxanes having terminal silanol groups and/or polydimethylsiloxanes having terminal alkoxy and silanol groups and/or amine-functionalized siloxanes containing silanol groups or alkoxy and silanol groups, are preferably reacted with a dialkoxy and/or trialkoxysilane, which has a radical formula

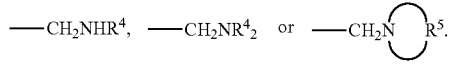

Accordingly, in formula (I), "fSiloxane" stands for a radical derived from an amine-functionalized siloxane.

Trialkoxysilanes or a mixture of dialkoxy and trialkoxysilanes are particularly preferably used, wherein the use of trialkoxysilanes alone is particularly preferred. At least partially crosslinked polyorganopolysiloxanes are obtained when using trialkoxysilanes or a mixture of dialkoxy and trialkoxysilanes, irrespective of the structure of the siloxanes used and the position of the alkoxy and/or silanol groups in the siloxanes. In a more preferred embodiment, the cosmetic agent contains crosslinked polyorganosiloxanes. In a most preferred embodiment, the cosmetic agent contains crosslinked polyorganosiloxanes resulting from the reaction of siloxanes and trialkoxysilanes.

Preferred examples of the dialkoxy or trialkoxysilanes used comprise:
diethylaminomethylmethyldimethoxysilane,
dibutylaminomethyltriethoxysilane,
dibutylaminomethyltributoxysilane,
cyclohexylaminomethyltrimethoxysilane,
cyclohexylaminomethyltriethoxysilane,
cyclohexylaminomethyl methyldiethoxysilane,
anilinomethyltriethoxysilane,
anilinomethylmethyldiethoxysilane,
morpholinomethyltriethoxysilane,
morpholinomethyltrimethoxysilane,
morpholinomethyltriisopropoxysilane,
3-dimethylaminopropyl-aminomethyltrimethoxysilane,
morpholinomethyltributoxysilane,
morpholinomethyltrialkoxysilane, wherein the alkoxy radical is a C$_1$-C$_4$ alkoxy radical, in
particular a mixture of methoxy and ethoxy radical,
piperazinomethyltriethoxysilane,
piperidinomethyltriethoxysilane and
partial hydrolyzates thereof.

A particularly preferred silane is morpholinomethyltriethoxysilane.

A particularly preferred amine-functionalized siloxane is a copolymer of 3-(2-aminoethylamino) propylmethylsiloxy and dimethylsiloxy units having silanol groups or alkoxy and silanol groups.

A method is particularly preferred in which the polyorganosiloxane used is at least one compound known by the INCI name Amodimethicone/Morpholinomethyl Silsesquioxane Copolymer. This polyorganosiloxane is commercially available under the name Belsil® ADM 8301 E (ex Wacker). The raw material constitutes a microemulsion and has the following components: Amodimethicone/Morpholinomethyl Silsesquioxane Copolymer, Trideceth-5, glycerol, phenoxyethanol and water.

The use of the polyorganosiloxanes described above is preferably carried out as aqueous suspensions or aqueous emulsions of polyorganosiloxanes. The dispersions can contain one or more surfactants as dispersants. The surfactants can be of any type, ionic and/or nonionic. Alternatively, inorganic solids such as silicic acids and/or bentonites can be used as dispersants. The mean particle size of the polyorganosiloxanes measured by employing light scattering in the dispersions is preferably in the range from about 0.001 to about 100 μm, more preferably from about 0.002 to about 10 μm. The pH values can vary from about 1 to about 14. The pH value is preferably from about 3 to about 9, more preferably from about 5 to about 8.

The cosmetic compositions used in the method in step i. preferably contain, based on their weight, from about 90 to about 98.5 by weight of water.

It has been shown that the protective effect of the cosmetic composition applied in step i. can be further improved when further certain nonionic components are included. In addition, these nonionic components have positive effects on the storage stability of the pretreatment agent.

Nonionic components which are particularly suitable herein are ethoxylates of decanol, undecanol, dodecanol, tridecanol, myristyl alcohol, cetyl alcohol and/or stearyl alcohol. Ethoxylated tridecanols have proven particularly suitable. Particularly preferred are branched ethoxylated tridecanols, in particular branched tridecanols having from 3 to 5 ethylene oxide units and/or from about 10 to about 15 ethylene oxide units in the molecule.

Cosmetic compositions used in step i. preferably contain, based on their weight, further branched, ethoxylated tridecanol (INCI name: Trideceth-5) or α-isotridecyl-w-hydroxypolyglycol ether (INCI name: Trideceth-10) or mixtures thereof.

Particularly preferred pretreatment agents contain, each based on their weight, from about 0.01 to about 5% by weight, and more preferably from about 0.1 to about 0.5% by weight of branched, ethoxylated tridecanol.

Extremely preferred pretreatment agents contain, based on their weight, from about 0.1 to about 0.5% by weight of Trideceth-5 and Trideceth-10.

It has been shown that the protective effect of the cosmetic composition applied in step i. is particularly high when applied in the form of a microemulsion.

The cosmetic composition used in step i. can contain further ingredients.

Preference is given here to the use of polyvalent alcohols which have moisturizing properties. Preference is given here to pretreatment agents as contemplated herein which contain at least one polyvalent alcohol, preferably selected from the group of sorbitol and/or glycerol and/or 1,2-propylene glycol or mixtures thereof, in a total amount from about 0.05 to about 15% by weight, preferably from about 0.1 to about 10% by weight, particularly preferably from about 0.15 to about 5% by weight and in particular from about 0.15 to about 1% by weight, each based on the weight of the cosmetic composition.

For certain application areas, it can be advantageous to use only one of the three preferred polyvalent alcohols mentioned above. In most cases, glycerol is preferred.

Further suitable ingredients comprise preservatives and perfume.

The pretreatment agent, which is applied in method step i. of the method, can be formulated as a low-viscosity water-based emulsion, as a spray, as a cream, gel, lotion, paste, shampoo or conditioner. Preferably, the pretreatment agent is a low viscosity microemulsion which is poured over the keratinic fibers. The polyorganosiloxanes of the formula (I) form a thin layer ("monolayer") on the fibers on contact with keratinic fibers. Mechanical forces, such as working in of the pretreatment agent with a comb, or structures (for example, thixotropic structures) within the pretreatment agent can destroy and/or hinder the formation of this thin film. Accordingly, it is preferred that the cosmetic composition used as pretreatment agent in the method, have, at about 20° C., a viscosity of less than about 200 mPas, preferably less than about 150 mPas and most preferably less than about 100 mPas (each measured with a Haake Roto Visco 1 Double Gap Cylinder System DG43).

The method comprises applying the pretreatment agent to keratinic fibers and subjecting them to a chemical treatment with an oxidizing agent or a reducing agent within a period of from about 5 seconds to about 24 hours.

A big advantage of the pretreatment agents used in step i. is that they are not only effective when they are applied immediately before the chemical treatment, but can be used up to about 24 hours before, without the fear of the effect being weakened by external influence. In this way it is possible, for example, to perform step i. of the method in the morning after hair washing and the chemical treatment only in the evening.

Preferred methods are exemplified in that the period between the method steps i. and ii. is from about 5 seconds to about 20 minutes, preferably from about 30 seconds to about 10 minutes, more preferably from about 1 to about 5 minutes.

Further preferred methods are exemplified in that in method step i., applied pretreatment agent can act on the hair for a period of from about 5 seconds to about 120 minutes, preferably from about 10 seconds to about 10 minutes, before method step ii. is started.

Preferably, the keratinic fibers, in step ii., are subjected to a chemical treatment in the form of an oxidative dyeing, an oxidative lightening, a chemical smoothing and/or a permanent wave treatment.

In a further preferred embodiment, the method is exemplified in that step ii. comprises the application of a lightening agent which contains at least one oxidizing agent.

In a further preferred embodiment, the method is exemplified in that step ii. comprises the application of a colorant which preferably contains at least one developer type oxidation dye precursor and at least one coupler type oxidation dye precursor and at least one oxidizing agent.

Preferred oxidizing agents are selected from peroxo compounds, preferably selected from hydrogen peroxide, solid addition compounds of hydrogen peroxide to inorganic or organic compounds, such as sodium perborate, sodium percarbonate, magnesium percarbonate, sodium percarbamide, polyvinylpyrrolidone n $H_2O_2$ (n is a positive integer greater than 0), urea peroxide and melamine peroxide, further selected from diammonium peroxodisulfate (also referred to as ammonium persulfate), disodium peroxodisulfate (also referred to as sodium persulfate) and dipotassium peroxodisulfate (also referred to as potassium persulfate) and mixtures of these oxidizing agents.

Very particularly preferred oxidizing agents are aqueous hydrogen peroxide solutions. The concentration of a hydrogen peroxide solution is determined, on the one hand, by the legal requirements and, on the other hand, by the desired effect; preferably from about 6-12% by weight solutions in water are used.

Preferred methods are exemplified in that the chemical hair treatment agent used in step ii., based on its weight, contains from about 0.5 to about 12% by weight, preferably from about 2 to about 10% by weight, particularly preferably from about 3 to about 6% by weight of hydrogen peroxide (calculated as about 100% $H_2O_2$).

A further preferred method as contemplated herein is exemplified in that in step ii., the hair treatment agent with oxidizing agent is rinsed from the keratinic fibers after a time of from about 5 to about 60 minutes, preferably from about 30 to about 45 minutes.

In a further preferred embodiment, the method is exemplified in that step ii. comprises the application of a smoothing agent which contains at least one oxidizing agent.

So-called basic ("lye-based") and/or non-basic (no-lye) relaxers are often used as reducing agents in smoothing agents. Basic relaxers are mostly preparations based on sodium hydroxide. The non-basic relaxers are usually based on potassium or lithium hydroxides and in particular guanidinium hydroxide.

In a further preferred embodiment, the method is exemplified in that step ii. comprises the application of a permanent wave agent which contains at least one reducing agent.

Preferred reducing agents for permanent waving agents comprise sulfites, preferably alkali metal, ammonium and/or alkanolammonium salts of sulfurous acid and of disulfurous acid, in particular sodium sulfite ($Na_2SO_3$) and/or sodium disulfite ($Na_2S_2O_5$), mercaptans, preferably bunte salts, thioglycolic acid, thiolactic acid, thiomalic acid, mercaptoethanesulfonic acid and salts and esters thereof, cysteamine or cysteine. The alkali or ammonium salts of thioglycolic acid and/or thiolactic acid are preferably included in permanent wave agents.

It can be preferred in both cases that after rinsing the treatment agent containing a reducing agent, a fixing agent containing an oxidizing agent is applied to the fibers and rinsed again after a contact time.

In a further, preferred embodiment of the method, after step ii. in a step iii. a further cosmetic composition is applied as a post-treatment agent to the keratinic fibers, wherein the further cosmetic composition has a pH value in the range from about 3 to about 5 and contains from about 0.01 to about 10% by weight of a polyvalent metal salt, wherein the metal salt is selected from the group of strontium salts, zirconium salts, hafnium salts, titanium salts, tin salts, aluminum salts, bismuth salts, lanthanum salts, calcium salts, magnesium salts and mixtures thereof.

The keratinic fibers treated with this further cosmetic composition have a stronger internal structure, which manifests itself in a higher denaturation temperature, an increased tear resistance and a reduced swelling in water. This applies in particular to application to oxidatively damaged, keratinic fibers.

It has been found that it is particularly effective and the strengthening of the internal structure is particularly high when the further cosmetic composition contains lanthanum maleate, lanthanum chloride and/or aluminum lactate.

The further cosmetic composition furthermore preferably contains an aqueous or an aqueous-alcoholic carrier. Furthermore, the further cosmetic composition can preferably be an organic acid selected from the group of tartaric acid, citric acid, maleic acid, fumaric acid, salicylic acid, lactic acid, malic acid, amino acids and mixtures thereof.

EXAMPLES

Hair strands were immersed for one minute in an aqueous composition that contained
about 0.1% by weight of Amodimethicone/Morpholinomethyl Silsesquioxane Copolymer,
about 0.15% by weight of glycerol,
about 0.25% by weight of Trideceth-5 and Trideceth-10, and
Water (ad 100).

The hair strands were then dried, a freshly prepared dye cream oxidizing agent mixture was applied to the strands and allowed to act for about 30 minutes. The colorant was then rinsed with water and the hair combed and possibly dried.

Pretreatment with the aqueous composition containing at least one compound known by the INCI name Amodimethicone/Morpholinomethyl Silsesquioxane Copolymer made it possible to markedly reduce hair damage compared to oxidative dyeing without pretreatment. The pretreatment with the aqueous composition, comprising about 0.1% by weight Amodimethicone/Morpholinomethyl Silsesquioxane Copolymer, prevents a decrease of the contact angle of the hair after the oxidation treatment to values between about 40° to about 80° and leads to contact angles of greater than about 95° after the oxidation treatment. The determination of the contact angle was carried out by the Wilhelmy method.

An additional post-treatment with an aqueous composition having a pH value in the range from about 3 to about 5 and containing about 1.3% by weight aluminum lactate, additionally leads to the strengthening of the inner hair structure, in particular in oxidatively damaged hair.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

What is claimed is:

1. A method for the chemical treatment of keratinic fibers, comprising:
   i. applying a cosmetic composition to keratinic fibers as a pretreatment, and
   ii. chemically treating the keratinic fibers with an oxidizing agent and/or a reducing agent within a period of from about 5 seconds to about 24 hours after step i, wherein;
   the cosmetic composition, based on its total weight, comprises:
   from about 0.01 to about 4.00% by weight of a polyorganosiloxane known by the INCI name Amodimethicone/Morpholinomethyl Silsesquioxane Copolymer;
   from about 0.01 to about 5% by weight of a mixture of Trideceth-5 and Trideceth-10;
   from about 0.1 to about 10% by weight of glycerol; and
   water.

2. The method according to claim 1, wherein chemically treating the keratinic fibers, in step ii, comprises chemically treating the keratinic fibers to a chemical treatment in the form of an oxidative dyeing, an oxidative lightening, a chemical smoothing and/or a permanent wave treatment.

3. The method according to claim 1, further comprising:
   iii. applying a further cosmetic composition to the keratinic fibers as a post-treatment agent after step ii, wherein the further cosmetic composition has a pH value in the range of from about 3 to about 5, wherein the further cosmetic composition comprises from about 0.01 to about 10% by weight of a polyvalent metal salt, based on a total weight of the further cosmetic composition, wherein the metal salt is selected from the group of strontium salts, zirconium salts, hafnium salts, titanium salts, tin salts, aluminum salts, bismuth salts, lanthanum salts, calcium salts, magnesium salts, and mixtures thereof.

4. The method according to claim 3, wherein the further cosmetic composition comprises lanthanum maleate, lanthanum chloride and/or aluminum lactate.

5. The method according to claim 1, wherein; step i. further comprises not rinsing the cosmetic composition out of the keratinic fibers before step ii; and/or
   the method further comprises dying the keratinic fibers after performing the treatment step i optionally by supplying warm air to the keratinic fibers.

6. The method according to claim 1 wherein: the cosmetic composition further comprises an additional branched tridecanols having from 3 to 5 ethylene oxide units and/or from about 10 to about 15 ethylene oxide units in the molecule.

7. The method according to claim 1 wherein: the cosmetic composition further comprises an additional polyvalent alcohol selected from the group of sorbitol, 1,2-propylene glycol, and mixtures thereof that is present in the cosmetic composition in a total amount of from about 0.1 to about 10% by weight, based on the weight of the cosmetic composition..

8. The method of claim 1 wherein the cosmetic composition comprises:
   about 0.1% by weight of the polyorganosiloxane;
   about 0.25% by weight of the Trideceth-5 and Trideceth-10; and
   about 0.15% by weight of the glycerol.

9. The method of claim 8 wherein step (ii) is further defined as chemically treating the keratinic fibers with the oxidizing agent, the method further comprises the step of rinsing the keratinic fibers after step (ii) and prior to optional post-treatment, and the method optionally further comprises the step of drying the keratinic fibers before and/or after step (ii).

10. The method of claim 1 wherein the cosmetic composition consists of:
    about 0.1% by weight of the polyorganosiloxane;
    about 0.25% by weight of the Trideceth-5 and Trideceth-10;
    about 0.15% by weight of the glycerol; and
    a balance of the water.

11. The method of claim 10 wherein step (ii) is further defined as chemically treating the keratinic fibers with the oxidizing agent, the method further comprises the step of rinsing the keratinic fibers after step (ii) and prior to optional post-treatment, and the method optionally further comprises the step of drying the keratinic fibers before and/or after step (ii).

12. The method of claim 1 wherein
the cosmetic composition comprises:
    about 0.1% by weight of the polyorganosiloxane;
    about 0.25% by weight of the Trideceth-5 and Trideceth-10;
    about 0.15% by weight of the glycerol; and
step (ii) is further defined as chemically treating the keratinic fibers with the oxidizing agent for a period of about 30 minutes after step (i).

13. The method of claim 12 further comprising the step of rinsing the keratinic fibers after step (ii) and prior to optional post-treatment and optionally further comprising the step of drying the keratinic fibers before and/or after step (ii).

14. The method of claim 1 wherein
the cosmetic composition consists of:
    about 0.1% by weight of the polyorganosiloxane;
    about 0.25% by weight of the Trideceth-5 and Trideceth-10;
    about 0.15% by weight of the glycerol; and
    a balance of the water; and
step (ii) is further defined as chemically treating the keratinic fibers with the oxidizing agent for a period of about 30 minutes after step (i).

15. The method of claim 14 further comprising the step of rinsing the keratinic fibers after step (ii) and prior to optional post-treatment and optionally further comprising the step of drying the keratinic fibers before and/or after step (ii).

16. The method of claim 1 wherein
the cosmetic composition comprises:
    about 0.1% by weight of the polyorganosiloxane;
    about 0.25% by weight of the Trideceth-5 and Trideceth-10; and
    about 0.15% by weight of the glycerol;
step (ii) is further defined as chemically treating the keratinic fibers with the oxidizing agent for a period of about 30 minutes after step (i); and
the method further comprises applying a post-treatment with an aqueous composition having a pH value of from about 3 to about 5 and comprising about 1.3% by weight aluminum lactate.

17. The method of claim 16 further comprising the step of rinsing the keratinic fibers after step (ii) and prior to post-treatment and optionally further comprising the step of drying the keratinic fibers before and/or after step (ii).

18. The method of claim 1 wherein
the cosmetic composition consists of:
    about 0.1% by weight of the polyorganosiloxane;
    about 0.25% by weight of the Trideceth-5 and Trideceth-10;
    about 0.15% by weight of the glycerol; and
    a balance of the water;
step (ii) is further defined as chemically treating the keratinic fibers with the oxidizing agent for a period of about 30 minutes after step (i); and
the method further comprises applying a post-treatment with an aqueous composition having a pH value of from about 3 to about 5 and comprising about 1.3% by weight aluminum lactate.

19. The method of claim 18 further comprising the step of rinsing the keratinic fibers after step (ii) and prior to post-treatment and optionally further comprising the step of drying the keratinic fibers before and/or after step (ii).

* * * * *